United States Patent [19]

Rao et al.

[11] Patent Number: 4,537,726

[45] Date of Patent: Aug. 27, 1985

[54] MULTI-STAGE PROCESS WITH ADIABATIC REACTORS FOR THE PREPARATION OF ISOCYANATES

[75] Inventors: Velliyur N. M. Rao, Wilmington, Del.; George E. Heinsohn, Elkton, Md.

[73] Assignee: E. I. Du Pont de Nemours and Company, Wilmington, Del.

[21] Appl. No.: 669,850

[22] Filed: Nov. 9, 1984

[51] Int. Cl.³ .......................................... C07C 118/04
[52] U.S. Cl. ................................................ 260/453 P
[58] Field of Search ..................................... 260/453 P

[56] References Cited

U.S. PATENT DOCUMENTS 4,207,251  6/1980  Heyboer ........................ 260/453 P Primary Examiner—Dolph H. Torrence

[57] ABSTRACT

The process in which organic isocyanates are prepared by the oxidative dehydrogenation of the corresponding formamides is improved by operating the process in at least two adiabatic reaction stages in series where no more than 0.7 equivalent of oxygen is fed to the first stage.

8 Claims, No Drawings

MULTI-STAGE PROCESS WITH ADIABATIC REACTORS FOR THE PREPARATION OF ISOCYANATES

BACKGROUND OF THE INVENTION

U.S. Pat. No. 4,207,251 discloses the gas phase production of $C_1$-$C_{24}$ organo-isocyanates by oxidative dehydrogenation of the corresponding N-monosubstituted formamides. This reaction is extremely exothermic, and consequently some method of temperature control or heat removal during the reaction has been employed to maintain the reaction temperature below that which would accelerate side reactions or actual decomposition of the isocyanate product. U.S. Pat. No. 4,207,251, for example, discloses the use of small diameter reactors or the introduction of relatively large volumes of an inert gas to the reaction mixture to absorb the heat liberated during the reaction. Disadvantages attend both of these methods, however. Small-diameter reactors that are designed for cooling are expensive and have relatively high surface-area/volume ratios, which often necessitates the use of several reactors in parallel, an arrangement which is difficult to operate. The use of an inert heat sink at the high volumes disclosed in the patent (over 50 volumes of inert gas per volume of oxygen), presents difficulty and expense in separation of the desired product. The improvement of the present invention eliminates the need for active cooling of the reactors and permits the reduction in volume, or entire elimination, of the inert gas.

SUMMARY OF THE INVENTION

The present invention provides an improved process for the preparation of isocyanates of the formula $R-(NCO)_n$ where R is a $C_1$-$C_{10}$ alkyl, cycloalkyl, aryl, alkaryl, or aralkyl group and n is 1 or 2, by reacting a corresponding formamide of the Formula $R(NH-CO-H)_n$ with oxygen or an oxygen-containing gas at 400°-700° C. in the presence of a silver catalyst, wherein the improvement comprises performing the reaction in at least two essentially adiabatic reaction stages in series and wherein the improvement is characterized by:

(a) introducing the formamide and up to 70% of the stoichiometric amount of oxygen to the first reaction stage at a temperature of 200°-350° C.;

(b) introducing additional oxygen to the reaction mixture effluent of each non-final stage; and (c) introducing the resultant reaction mixture of step (b) to the succeeding reaction stage at a temperature below 350° C.

DETAILED DESCRIPTION OF THE INVENTION

The present invention provides an improved manner of conducting the process for the preparation of isocyanates disclosed in U.S. Pat. No. 4,207,251. That process involves the gas phase oxidation of an N-monosubstituted formamide of the formula $R(NH-CO-H)_n$ where R is a substituted or unsubstituted alkyl, cycloalkyl, aryl, alkaryl, or aralkyl group and n is 1 or 2, to the corresponding isocyanate of the formula $R-(NCO)_n$. The oxidizing agent is oxygen, supplied to the reaction either pure or as part of an oxygen-containing gas, such as air. The reaction is performed at 300°-600° C. in the presence of a catalyst of copper and/or one or more metals of the groups IB and VIII of the 5th and 6th periods of the Periodic System of Elements. Details of the reaction, including reactants and process conditions, are provided in U.S. Pat. No. 4,207,251 and the disclosures of that patent are incorporated herein by reference as the context in which the present invention operates.

In the improved process of the present invention, the catalysts preferred for use contain silver and are either pure silver or a combination of silver and one of the other metals described as a catalyst for the oxidative dehydrogenation. Gold is preferred for use when the catalyst is to contain silver in combination with another metal.

It is preferred to use a catalyst in the form of crystals or sputtered (vapor deposited) or ion plated on an inert support. When either of the latter two forms is used, generally the silver or silver/metal combination will comprise from 0.05–50 weight percent of the total catalyst composition. Generally the catalyst support will be a hard, nonporous refractory particulate material, preferably ceramic, having a mean particle diameter in the range of from 0.1 micron to 0.5 centimeter. The support should have a surface area below about 20 square meters per gram and preferably less than 3 square meters per gram. Alumina and silica are the preferred catalyst supports, although other oxides such as ceria, yttria, zirconia, or titania can be used. These catalysts, and their method of preparation, are disclosed in U.S. Pat. No. 4,469,640 incorporated herein by reference.

The oxidative dehydrogenation of the described process evolves a considerable amount of heat, and the improvement of the present invention is directed towards controlling the heat so as to limit the temperature to which the reaction mixture rises. Specifically, it has been found that high conversion to the isocyanate can be achieved while maintaining temperature control by performing the reaction in two or more reaction stages in series and by providing to the first reaction stage less than the stoichiometric amount of oxygen relative to the amount of formamide. Additional oxygen is supplied to the succeeding stages to provide successively higher conversion of the formamide. The reaction mixture effluent from all but the last of the reaction stages is cooled to provide further temperature control, as described more fully below. In each stage, therefore, there is either excess reactant or previously-formed isocyanate product, which is introduced at a temperature below the desired maximum, to provide heat absorbing capacity.

According to the improved process of this invention, the oxidative dehydrogenation is performed in multiple stages in series. Although any number of sequential reactor stages can be used, little additional benefit in temperature control or overall yield is afforded by the use of more than four reactors. Preferably two or three reaction stages in sequence are used.

The formamide is vaporized, after which it and the oxygen or oxygen-containing gas are introduced to the first reactor. Preferably, the vaporized formamide is pre-mixed with the oxygen, and the mixture then introduced to the first reactor. The entirety of the formamide reactant is preferably introduced into the reaction series through the first stage. It is to be understood, however, that small amounts of additional formamide can be introduced interstage for make-up to succeeding reaction stages, but substantially all the formamide reactant, that is, at least about 90%, should be introduced to the first stage. As mentioned, preferably the entirety of the formamide is fed to the first stage.

The amount of oxygen entering the first stage with the formamide is no more than 70% of the stoichiometric amount, based on the formamide entering the first stage, and is usually in the range of about 25–70%. When three or four reactors are used in series, oxygen fed to the first stage is preferably 25–40% of the stoichiometric amount. When two reactors are used in series, it is preferred to use about 30–65% of the stoichiometric requirement of oxygen.

The feed of formamide and oxygen enters the first reaction stage in gas phase and at a temperature of about 200°–350° C. In the first and any succeeding reaction stages, the temperature at which the reaction is carried out is normally in the range of 400°–650° C. A temperature of 700° C. can be used, but normally tempeatures higher than this should be avoided to reduce the risk of yield-lowering side reactions and product decomposition. A reaction temperature of about 450°–625° C. is preferred.

The reaction mixture leaving the first stage, or any non-final reaction stage in the series, normally contains the isocyanate product, by-products (including water vapor), unreacted formamide, and possibly nitrogen (particularly if air is the source of oxygen employed) or some other inert gas, discussed below. To this reaction mixture is further added additional oxygen so that any previously unreacted formamide will be converted in the succeeding reaction stages. This procedure is followed for the reaction mixture leaving each non-final reaction stage. The amount of oxygen added to the reaction mixture as it leaves any one non-final stage is dependent upon the cumulative amount introduced to the preceding stage or stages and upon the number of reaction stages remaining. Generally, however, sufficient oxygen is added at each of these interstage points so that the cumulative amount of oxygen that has been added to the system as the reaction mixture is introduced to the final reaction stage is at least equal to, preferably in excess of, the stoichiometric requirement of oxygen based on the total formamide feed.

For example, when two reaction stages are to be used, it is preferred to feed 0.3–0.65 equivalent of oxygen to the first stage and about 0.45–0.75 equivalent of oxygen, based on the original formamide feed, to the final, second stage. The total amount of oxygen should be at least one full equivalent, based on the total amount of formamide fed to the reaction system. When three reaction stages are to be used, it is preferred to feed 0.25–0.4 equivalent of oxygen to the first stage and about 0.35–0.5 equivalent, based on the original formamide feed, to each of the next two stages, the total being at least one full equivalent based on the total amount of formamide fed to the reaction system.

To provide heat absorbing capacity for temperature control for the second and any succeeding reaction stages, the reaction mixture effluent of the first stage and each of the other non-final stages, if any, must be cooled before being introduced to the next stage. This cooling must be to a temperature that is sufficiently low to provide heat absorbing capacity sufficient to maintain the operating temperature of the next reaction stage below 700° C. This temperature is preferably 350° C. or lower, and most preferably about 225°–300° C. The oxygen or oxygen-containing gas that is added interstage, as discussed above, is normally at a lower temperature than is the reaction mixture effluent to which it is added, and the resultant reaction mixture might be brought to the proper temperature by this oxygen addition alone. Normally, however, further cooling will be required, and conventional heat exchange equipment, such as standard shell-and-tube exchangers, can be used to cool the reaction mixture before introducing it to the next stage.

Through this improved multi-stage process, the heat liberated by the exothermic reaction is controlled and the operating temperature of each reactor maintained within the desired range. By providing less than a full equivalent of oxygen to the first stage, only partial conversion of the formamide takes place, and not all the potential heat is evolved. The excess unreacted formamide provides capacity to absorb the heat that is liberated, thereby preventing the reaction temperature from rising above the desired levels. In the succeeding reaction stages, this heat absorbing capacity is provided by the isocyanate product and water vapor produced in the preceding stage or stages. The invention thereby allows the substitution of less costly interstage cooling equipment in place of other cooling strategies, such as cooling equipment on the reactors themselves or use of large volumes of inert gas.

The reactors are preferably insulated but need not be, and the dissipation of some reaction heat to the surroundings does not affect the operation of the process. Each reaction stage is therefore essentially adiabatic, that term being used here to mean that the reaction occurs without active removal of heat from the reaction stage itself.

The improved process of this invention is conducted in a continuous manner. The reaction mixture effluent of the final reaction stage is subjected to a separation procedure, which itself can be conducted continuously or batchwise, to isolate the isocyanate product. Continuous separation is preferred. Separation procedures are known in the art, and those disclosed in U.S. Pat. No. 4,207,251, for example, can be used.

The reaction, conducted according to the improved process of this invention, can be carried out in the presence of an inert gas, preferably nitrogen, which provides additional heat capacity. Generally, however, no more than 15 volumes of inert gas per volume of oxygen are necessary. Preferably, about 4–12 volumes of inert per volume of oxygen are used. The inert gas can be introduced to any or all of the reaction stages, and can be mixed with the reactants, as when oxygen is supplied in the form of air, or can be introduced separately. When the inert gas is introduced separately, it is preferred to introduce substantially all of it to the first stage.

The absolute pressure of the gas phase mixture, including inerts if any, is not critical and can be varied from about 100 to 1000 kPa in the reaction stages. It is preferred that the reaction be carried out at an absolute pressure of about 1 atmosphere (100 kPa).

The benefits of this invention are obtainable when conducting the oxidative dehydrogenation to produce any of the $C_1$–$C_{24}$ organic isocyanates as disclosed in U.S. Pat. No. 4,207,251. Particularly suitable are the $C_1$–$C_{10}$ alkyl, cycloalkyl, aryl, alkaryl, or aralkyl isocyanates described therein. Most preferred for production according to the improved process of this invention is methyl isocyanate from the oxidative dehydrogenation of monomethyl formamide. Methyl isocyanate is used in the production of certain insecticides including S-methyl-N-[(methylcarbamoyl)oxy] thioacetimidate (methomyl).

EXAMPLES 1-7

The general procedure employed in Examples 1-7 was as follows: Monomethyl formamide (MMF) was continuously vaporized and mixed in a heated vessel with air and, in some examples as noted, nitrogen. This gas mixture was then heated to 230° C. and fed continuously to a reactor at gradually increasing rates until a rate of 35 grams/hour of MMF, with the corresponding amounts of air and nitrogen, as shown in the table below, was established. The reactor was a quartz tube reactor (10 mm inside diameter; 18 cm in length) containing 8.0 grams of crystalline silver catalyst, at a catalyst bed depth of 2.5 cm. The reaction tube was equipped with a thermocouple to measure the temperature of the catalyst bed, and the bed was equipped with an electric heater to initially elevate the temperature to a level sufficient to start the reaction. When reaction was proceeding steadily, the electric heater was adjusted so as to make up the heat lost to the surroundings from the uninsulated reaction tube, to simulate adiabatic conditions of commercial-size reactors. The reaction mixture effluent of the first reactor was mixed with additional air, charged at ambient temperature, and the interstage temperature of the resultant mixture was recorded. In each case, the addition of air, and the loss of heat through the walls of the interstage piping, caused the temperature of the resultant mixture to drop to between 240° C. and 265° C. The reaction mixture was then passed through a second reaction tube which was equipped and operated identically to the first reaction tube. The entire reaction sequence was operated at about atmospheric pressure. The reaction mixture effluent of the second reactor was cooled to about 240° C. and analyzed for methyl isocyanate (MIC) content and MMF conversion. The process conditions and results are summarized in the Table.

| Example | Reactor 1 Equiv. Oxygen[a] | Reactor 1 Temp. (°C.) | Reactor 2 Equiv. Oxygen[a] | Reactor 2 Temp. (°C.) | $N_2/O_2$[b] | Overall MMF Conversion[c] | MIC Obtained[d] |
|---|---|---|---|---|---|---|---|
| 1 | 0.5 | 550 | 0.6 | 565 | 7.0 | 90 | 86 |
| 2 | 0.5 | 525 | 0.6 | 530 | 12.5 | 85 | 87 |
| 3 | 0.5 | 510 | 0.7 | 525 | 12.0 | 93 | 88 |
| 4 | 0.5 | 565 | 0.75 | 575 | 4.0 | 95 | 84 |
| 5 | 0.6 | 575 | 0.7 | 555 | 8.0 | 90 | 85 |
| 6 | 0.6 | 550 | 0.8 | 540 | 11.0 | 93 | 89 |
| 7 | 0.6 | 560 | 1.0 | 570 | 8.0 | 97 | 87 |

[a]Equivalent amount of oxygen, in air, charged to the reactor indicated, based on amount of MMF originally fed to Reactor 1.
[b]Total volume of nitrogen fed to the reactors, separately or in air, per total volume of oxygen fed to the reactors.
[c]Moles of MMF consumed per mole of MMF fed, expressed as percentage.
[d]Moles of MIC in effluent of Reactor 2 per mole of MMF consumed overall, expressed as percentage.

What is claimed is:

1. An improved process for the preparation of isocyanates of the formula R—(NCO)$_n$ where R is a $C_1$-$C_{10}$ alkyl, cycloalkyl, aryl, alkaryl, or aralkyl group and n is 1 or 2, by reacting a corresponding formamide of the Formula R(NH—CO—H)$_n$ with oxygen or an oxygen-containing gas at 400°-700° C. in the presence of a silver catalyst, wherein the improvement comprises performing the reaction in at least two essentially adiabatic reaction stages in series and wherein the improvement is characterized by:
    (a) introducing the formamide and up to 70% of the stoichiometric amount of oxygen to the first reaction stage at a temperature sufficiently low to maintain the temperature of the reaction in the first stage at 700° C. or below;
    (b) introducing additional oxygen to the reaction mixture effluent of each non-final stage; and
    (c) introducing the resultant reaction mixture of step (b) to the succeeding reaction stage at a temperature sufficiently low to maintain the temperature of the reaction in the succceeding stage at 700° C. or below.

2. An improved process for the preparation of isocyanates of the formula R—(NCO)$_n$ where R is a $C_1$-$C_{10}$ alkyl, cycloalkyl, aryl, alkaryl, or aralkyl group and n is 1 or 2, by reacting a corresponding formamide of the Formula R(NH—CO—H)$_n$ with oxygen or an oxygen-containing gas at 400°-700° C. in the presence of a silver catalyst, wherein the improvement comprises performing the reaction in at least two essentially adiabatic reaction stages in series and wherein the improvement is characterized by:
    (a) introducing the formamide and up to 70% of the stoichiometric amount of oxygen to the first reaction stage at a temperature of 200°-350° C.;
    (b) introducing additional oxygen to the reaction mixture effluent of each non-final stage; and
    (c) introducing the resultant reaction mixture of step (b) to the succeeding reaction stage at a temperature below 350° C.

3. The process of claim 2 wherein the reaction is performed in 3-4 reaction stages in series and in which 25-40% of the stoichiometric amount of oxygen is introduced to the first stage.

4. The process of claim 2 wherein the reaction is performed in 2 stages in series and in which 30-65% of the stoichiometric amount of oxygen is introduced to the first stage.

5. The process of claim 2 wherein the reaction is carried out in the presence of an inert gas.

6. The process of claim 1, 2, 3, 4 or 5 which includes cooling the resultant reaction mixture of step (b).

7. The process of claim 1, 2, 3, 4 or 5 wherein the formamide is monomethyl formamide.

8. In a process for the preparation of methyl isocyanate by reacting monomethyl formamide with oxygen at a temperature of 450°-625° C. in the presence of a silver catalyst, the improvement comprising performing the reaction in two essentially adiabatic reaction stages in series wherein the improvement is characterized by
    (a) pre-mixing the monomethyl formamide and sufficient air to provide 30-65% of the stoichiometric amount of oxygen;
    (b) introducing the mixture of step (a) to the first reaction stage at a temperature of 200°-350° C.;
    (c) introducing to the reaction mixture effluent of the first stage sufficient additional air to provide an additional 35-75% of the stoichiometric amount of oxygen, based on the amount of monomethyl formamide introduced to the first stage;
    (d) cooling the resultant reaction mixture of step (c) to a temperature of 225°-300° C.; and
    (e) introducing the reaction mixture to the second reaction stage.

* * * * *